United States Patent [19]

Robinson et al.

[11] Patent Number: 4,784,589

[45] Date of Patent: Nov. 15, 1988

[54] PURIFICATION OF PERTUSSIS ANTIGENS

[75] Inventors: Andrew Robinson; Laurence I. Irons, both of Salisbury, England

[73] Assignee: Public Health Laboratory Service Board, London, England

[21] Appl. No.: 8,880

[22] Filed: Jan. 20, 1987

[30] Foreign Application Priority Data

Jan. 20, 1986 [GB] United Kingdom ................ 8601279

[51] Int. Cl.$^4$ ........................ A61K 39/10; C07K 3/12; C07K 3/28
[52] U.S. Cl. ..................................... 424/9 Q; 424/88; 530/396; 530/399; 530/406; 530/417; 530/825
[58] Field of Search .................... 424/88, 92; 530/825, 530/406, 417, 396, 399

[56] References Cited

U.S. PATENT DOCUMENTS

| | | | |
|---|---|---|---|
| 4,247,452 | 1/1981 | Irons et al. ........................... | 530/396 |
| 4,455,297 | 6/1984 | Syukuda et al. ................. | 530/406 X |
| 4,474,758 | 10/1984 | Kuo et al. ............................... | 424/92 |
| 4,551,429 | 11/1985 | Greenspan ......................... | 424/92 X |
| 4,563,303 | 1/1986 | Ginnaga et al. ...................... | 530/417 |
| 4,578,270 | 3/1986 | Csizer et al. ........................... | 424/92 |
| 4,687,738 | 8/1987 | Ginnaga et al. ................... | 424/92 X |
| 4,704,274 | 11/1987 | Sakuma et al. ....................... | 424/88 |

FOREIGN PATENT DOCUMENTS 0003916  9/1979  European Pat. Off. ............ 530/825

OTHER PUBLICATIONS

Infection and Immunity, 41, No. 1 (1983), 313-329, Sato et al.
The Lancet, Jan. 1984, Sato et al., 122-126.
Vaccine, vol. 3, Mar. 1985, 11-22, Robinson et al.

Primary Examiner—Howard E. Schain
Attorney, Agent, or Firm—Browdy and Neimark

[57] ABSTRACT

A process is provided for the production of lymphocytosis promoting factor (LPF), filamentous haemagglutinin (FHA) and at least one fimbrial agglutinogen from a liquid culture of Bordetella pertussis, which comprises the steps of (a) separating the culture into cellular and supernatant fractions, (b) concentrating the supernatant fraction, (c) fractionating the concentrated supernatant fraction to isolate LPF and FHA containing fractions, and (d) isolating at least one fimbrial agglutinogen from the cellular fraction. A vaccine composition may be produced by mixing so-produced LPF, FHA and fimbrial agglutinogens produced.

9 Claims, 2 Drawing Sheets

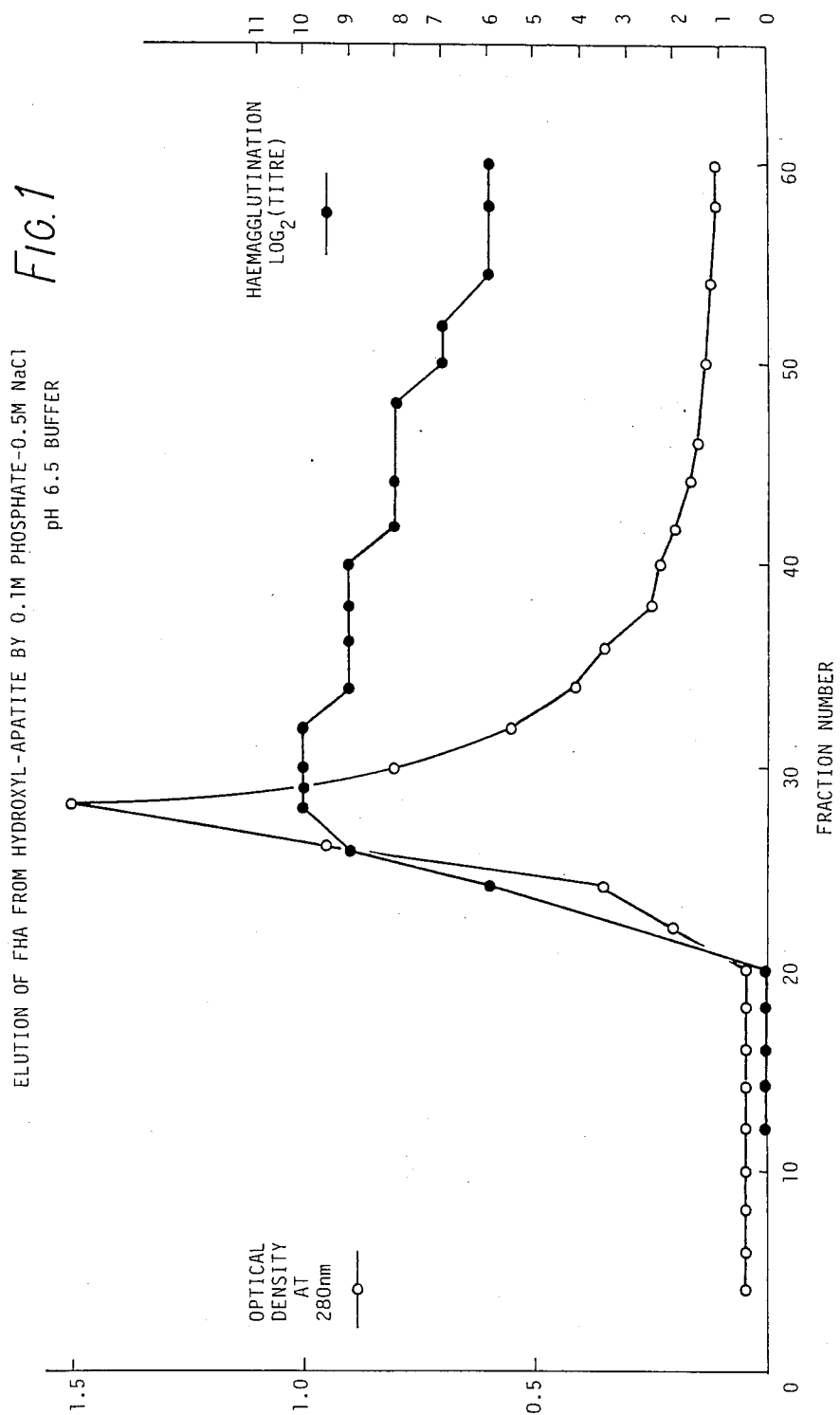

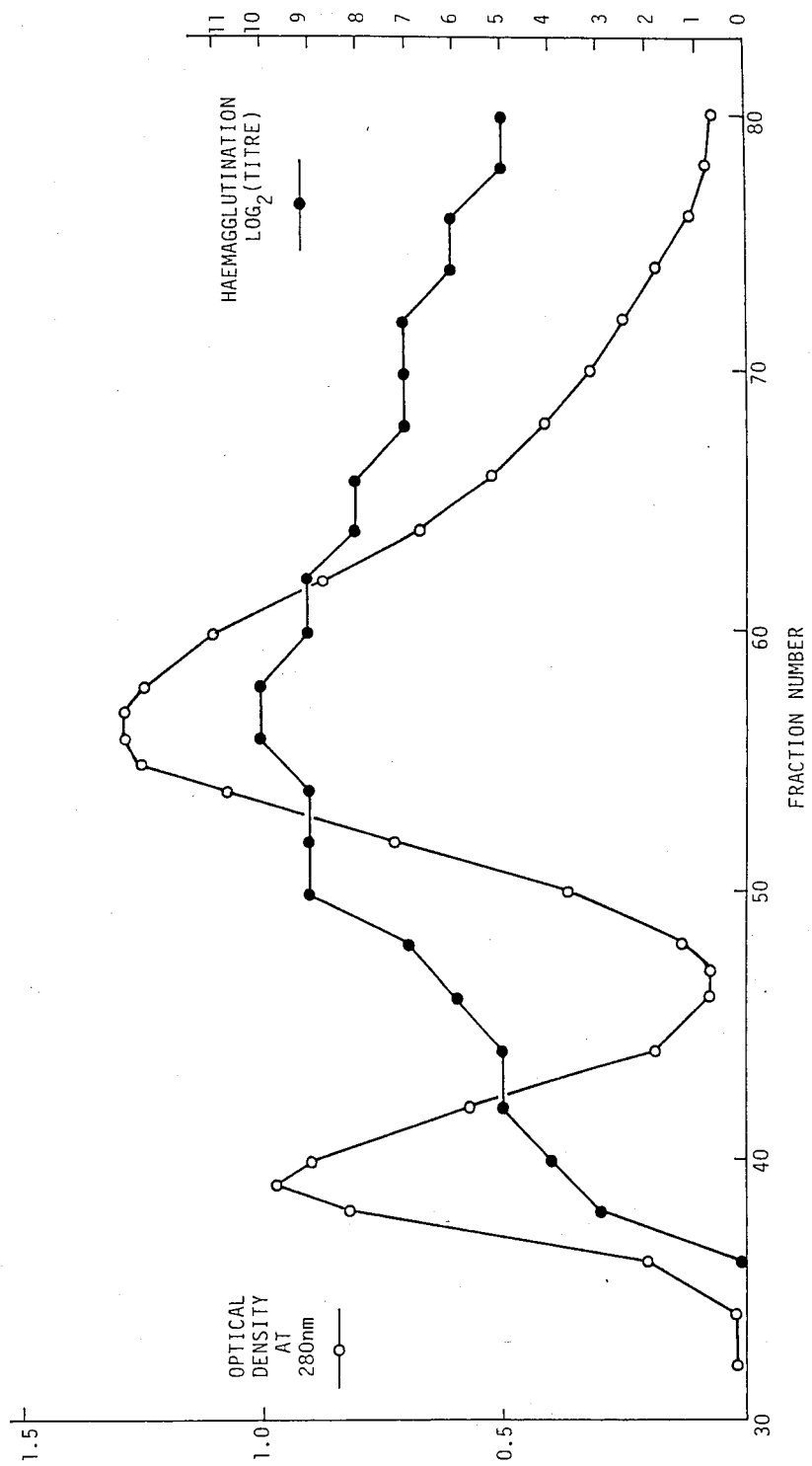

PURIFICATION OF PERTUSSIS ANTIGENS

This invention relates to a process for the production of antigenic substances for use in formulating vaccines against infection by Bordetella pertussis.

Hitherto, widespread use has been made of killed whole-cell Bordetella pertussis vaccines in the control of pertussis. Adverse reactions to whole-cell vaccines and the resulting reduced public acceptance of these vaccines has led to considerable research being carried out in an attempt to produce a safer acellular vaccine containing isolated pertussis antigens.

Three particular antigen fractions are regarded as being useful components of acellular vaccines, namely (1) lymphocytosis promoting factor (LPF), (2) filamentous haemagglutinin (FHA) and (3) fimbrial agglutinogens (fimbriae).

Included in the class of antigens represented by fraction (3), i.e. the fimbrial agglutinogens, are the agglutinogens referred to as "agglutinogens 2 and 3". (Agglutinogens 2 and 3 may also be referred to as "$Ag_{2+3}$"). Agglutinogens 2 and 3 may be regarded as consisting of fimbriae isolated from organisms bearing at least agglutinogen 2 and 3 antigens. (Agglutinogen 3 is referred to as "agglutinogen 6" by certain workers and it may be that agglutinogens 3 and 6 are the same).

Although procedures are known for isolating these fractions on a small scale, no procedures have hitherto been available for producing all three fractions separately and efficiently from cultures of Bordetella pertussis. Thus, for example, EP-A-No.0003916 describes a process for obtaining lymphocytosis promoting factor (LPF) by subjecting a liquid preparation derived from cells of Bordetella pertussis to affinity chromatography utilizing as a stationary phase a sialo-protein. However the liquid preparation which was used was derived from a homogenized cell paste and while the procedures described are efficient for the production of LPF, the patent is not directed to the separate isolation of filamentous haemagglutinin (FHA) and agglutinogens 2 and 3 ($Ag_{2+3}$).

Procedures have also been proposed for obtaining lymphocytosis promoting factor (LPF) and filamentous haemagglutinin (FHA) from the culture supernatant of Bordetella pertussis, for example Sato et al (Infection and Immunity, July 1983, Vol. 41, p. 313-320) describe the purification of LPF and FHA from culture supernatants by differential absorption on a hydroxyl apatite column.

These prior documents are not concerned, however, with the co-production of all three of lymphocytosis promoting factor (LPF), filamentous haemagglutinin (FHA) and fimbrial agglutinogens.

For the production of vaccine compositions comprising all three of these antigen fractions it would be desirable to obtain the three desired fractions in comparable yields since it may be advantageous for the fractions to be present in approximately equal proportions in the eventual vaccine.

According to the present invention there is provided a process for the production of lymphocytosis promoting factor (LPF), filamentous haemagglutinin (FHA) and at least one fimbrial agglutinogen from a liquid culture of Bordetella pertussis, which comprises the steps of (a) separating the culture into cellular and supernatant fractions,
(b) concentrating the supernatant fraction,
(c) fractionating the concentrated supernatant fraction to isolate LPF and FHA containing fractions, and
(d) isolating at least one fimbrial agglutinogen from the cellular fraction.

Preferably in step (d), fimbrial agglutinogens comprising at least agglutinogens 2 and 3 ($Ag_{2+3}$) are isolated from the cellular fraction. Optionally, the isolated agglutinogens additionally include one or more of agglutinogens 4, 5 and 6.

The invention also provides a process for the production of a vaccine composition comprising lymphocytosis promoting factor (LPF), filamentous haemagglutinin (FHA) and at least one fimbrial agglutinogen which comprises mixing (i) LPF, (ii) FHA and (iii) at least one fimbrial agglutinogen, said LPF, FHA and at least one fimbrial agglutinogen being produced by steps (a) to (d) described above and being detoxified prior to or subsequent to mixing. Preferably the fimbrial agglutinogens include at least agglutinogens 2 and 3 ($Ag_{2+3}$). The fimbrial agglutinogens may also include at least one of agglutinogens 4, 5 and 6.

By isolating the LPF, FHA and the at least one fimbrial agglutinogen in accordance with the invention it is possible to obtain these components from a single liquid culture in yields enabling their recombination in therapeutically effective quantities in vaccine compositions.

As indicated, in carrying out the process of the invention the supernatant fraction is concentrated prior to carrying out fractionation step (c) and surprisingly it has been found that by carrying this sequence of steps, i.e. with the concentration step (b) carried out after separation of the supernatant fraction from the cellular fraction, unacceptable losses of FHA can be avoided.

The separation of the culture into cellular and supernatant fractions is preferably carried out by centrifugation when the pH of the culture is greater than 7.0 and preferably at a pH greater than or equal to 8.0. Most preferably the pH of the culture is in the range of 7.5 to 9.0.

After centrifugation, the supernatant fraction is preferably concentrated so as to reduce its volume to less than 50% and preferably less than 25% of the original volume. Conveniently the concentration may be effected by any conventional dewatering means, for example by Pellicon concentration. Following the concentration step and prior to fractionating the supernatant into LPF and FHA containing fractions the supernatant is preferably subjected to membrane filtration to remove any residual organisms. Fractionation step (c) can then conveniently be carried out by contacting the supernatant with hydroxyl apatite, for example in a column, whereupon an FHA containing fraction is retained and an eluate comprising an LPF containing fraction can be recovered.

The LPF containing fraction may be purified by conventional protein fractionation techniques, for example by precipitating proteinaceous material by increasing the salt concentration using for example ammonium sulphate followed by extraction of the precipitate using a suitable buffer. The extract may then be dialysed and the dialysed LPF-containing solution so obtained may be further purified to remove other proteins and lipopolysacchoride, for example by the procedure described in EP-A-No. 0003916.

Thus, for example, the dialysed LPF-containing solution may be applied to a fetuin sepharose column and retained LPF eluted using a magnesium chloride buffer.

The thus purified LPF containing fraction may then be dialysed again, filtered and then subjected to a detoxifying procedure.

Purification of the FHA containing fraction may be achieved by eluting the fraction from the hydroxyl apatite adsorbent using buffers of increasing ionic strength followed by conventional protein purification steps including, for example, precipitation at high salt concentrations and chromatography. Finally, the purified FHA-containing fractions may be subjected to membrane filtration and then to a detoxifying step.

In order to isolate fimbrial agglutinogens, e.g. agglutinogens 2 and 3 ($Ag_{2+3}$) from the cellular fraction, the cells are preferably washed and then homogenized in a suitable buffer. Following centrifugation, the supernatant may then be subjected to conventional protein purification procedures in order to isolate a fraction comprising fimbrial agglutinogens. Thus, for example, a fimbrial agglutinogen-containing fraction may be precipitated by increasing the ionic strength of the solution, followed by one or more extractions with buffer, re-precipitations and dialysis. Finally, the purified fimbrial agglutinogen-containing fraction may be subjected to membrane filtration followed by a detoxifying step.

If desired the lipopolysaccharide content of the fimbrial agglutinogen fraction may be reduced by affinity chromatography, e.g. on a polymyxin-sepharose 4B column.

The detoxifying steps are preferably carried out by treating the LPF, FHA and fimbrial agglutinogen containing fractions individually or in combination with a conventional toxoiding agents such as, for example formaldehyde.

In order to produce vaccine compositions from the LPF, FHA and fimbrial agglutinogen fractions, these fractions are combined in therapeutically effective proportions and formulated into dosage units containing for example at least 1-5 and preferably at least 2 ug of each component per unit dose.

Conventional growth media may be employed to produce the liquid culture of Bordetella pertussis used as starting material in the process of the invention. However in order to produce commercially valuable yields of FHA it has been found to be desirable to use Stainer and Scholte's medium containing 2-6 mg/ml of dimethyl-B-cyclodextrin (MeCD), particularly in shaken cultures or stirred fermenters. Growth of the bulk culture may conveniently be carried out in 1 litre Thompson bottles containing 300 ml of medium or in 10 litre fermenters. A suitable strain of Bordetella pertussis is the Wellcome 28 strain which is of the 1.2.3 serotype. Other strains of a 1.2.3 serotype which produce adequate yields of antigens may be used.

The production of lymphocytosis promoting factor (LPF), filamentous haemagglutinin (FHA) and agglutinogens 2 and 3 ($Ag_{2+3}$) in accordance with the invention will now be described by way of example.

EXAMPLE

A culture of *Bordetella pertussis* was prepared as follows:

A freeze-dried ampoule of *B. pertussis,* strain Wellcome 28, was opened, the contents dispersed in sterile water and pipetted on to a charcoal agar plate containing 10% defibrinated horse blood. After incubation at 35° C. for 48 hours the organisms were subcultured on to several charcoal agar plates which were incubated at 35° C. for 48 hours.

The organisms were then scraped into several 250 ml conical flasks containing 100 ml Stainer and Scholte's medium supplemented with 1% casamino acids and 1 mg MeCD/ml. The flasks were shaken orbitally (180 rev./min) for 24 hours at 35° C. and then 5-10 ml transferred to each of 60 Thompson bottles containing 300 ml medium. The bottles were shaken on a gently reciprocating shaker at 35° C. for 48 hours before pooling the contents of the bottles and harvesting.

The resulting liquid culture of Bordetella pertussis was centrifuged in a Sorvall RC3B centrifuge for one hour at 5000 rpm. The supernatant was decanted and the cells stored at 4° C. for preparation of agglutinogens 2 and 3 ($Ag_{2+3}$).

The supernatant was concentrated using a Millipore Pellicon apparatus fitted with a 10,000 molecular weight cut-off filter. Eighteen liters of supernatant was concentrated to a volume of approximately 4 liters. The concentrate was then subjected to sterile filtration through a Gelman 0.2 um polysulphone mini capsule filter. 1. Purification of Filamentous Haemagglutinin (FHA)

Purification of the filamentous haemagglutinin (FHA) from the culture supernatant was achieved by consecutive steps of hydroxy apatite chromatography, ammonium sulphate precipitation and Sepharose CL-6B chromatography.

A. Hydroxylapatite Chromatography 400 g of spheroidal hydroxyapatite (BDH Chemicals Ltd) were suspended in 500 ml of 0.1M NaOH. The powder was allowed to settle for about 20 minutes at room temperature and excess liquid decantaed. The washing with sodium hydroxide was repeated twice, followed by repeated washing with distilled water until the pH of the eluate was about 8.0.

The washed powder was suspended in 500 mls of 0.01M phosphate buffer and after 20 minutes the buffer was decanted. The washing with phosphate buffer was repeated three times.

The washed hydroxylapatite was packed into a chromatography column equilibrated with 0.01M phosphate buffer at pH 8.0

The column was then connected to a reservoir containing the concentrated supernatant which was pumped through the column using a peristaltic pump at a flow rate of about 500 ml/hour. The eluate was retained for isolation of LPF (see below).

The retained FHA fraction was eluted from the column by washing successively with (i) 0.01M phosphate buffer at pH 8, (ii) 0.1M phosphate buffer at pH 8 and (iii) 0.1M phosphate-0.5M sodium chloride buffer at pH 6.5. During the final washing seventy 8 ml fractions were collected and the optical density at 280 mm of each fraction was recorded. Also, the haemagglutinating activity of alternate fractions was assayed using freshly washed goose erythrocytes. Fractions having a haemagglutinating titre (Log 2) greater than or equal to 7 were pooled. A record of the elution is shown in FIG. 1.

B. Ammonium Sulphate Precipitation

FHA was precipitated from the pooled fractions by adding ammonium sulphate to give a 30% saturated solution, followed by centrifugation. The supernatant was decanted and discarded and the precipitate was dissolved in 0.05M phosphate-0.5M sodium chloride buffer at pH 7.2 and dialysed against the same buffer. The dialysed suspension was centrifuged and the supernatant retained for subsequent purification.

C. Sepharose CL-6B Chromatography

The supernatant was then subjected to chromatography on Sepharose CL-6B gel which had previously been equilibrated with 0.05M phosphate-0.5M sodium chloride buffer at pH 7.2

The FHA was then eluted from the column using 0.05M phosphate-0.5M sodium chloride buffer at pH 7.2 and eighty 5 ml fractions were collected. The eluate fractions were monitored for protein and haemagglutinating activity in the manner described above and fractions having an haemagglutinating titre greater than or equal to 7 were pooled. A record of the elution is shown in FIG. 2. 2. Purification of LPF The eluate from the hydroxyapatite chromatography step was then treated for recovery of LPF.

A. Ammonium Sulphate Precipitation

In an initial step, impure LPF was precipitated by adding ammonium sulphate to give 74% saturated solution. The resulting suspension was centrifuged and the supernatant discarded. The precipitate was resuspended in 0.05M phosphate-0.05M sodium chloride buffer at pH 7.2. The suspension was then centrifuged at 15,000 rpm and the supernatant retained. The product was extracted a further four times using the same buffer and the resulting supernatants pooled.

B. Fetuin Sepharose Chromatography

The pooled supernatants were then dialysed against 0.05M phosphate-0.05M sodium chloride buffer at pH 7.2 and then subjected to chromatography on a fetuin sepharose gel which had been pre-equilibrated in 0.05M phosphate-0.05M sodium chloride buffer at pH 7.2. The column was then washed with the same buffer and the eluate discarded.

A purified LPF-containing fraction was then eluted from the column using 6.7 mM tris-0.013M sodium chloride/3M magnesium chloride buffer at pH 6.4 and thirty 50-drop fractions were collected. Fractions having an haemagglutinating titre greater than or equal to 7 were pooled and dialysed against 2 liters of 0.05Mtris HCl, IM NaCl buffer at pH 8.0. The LPF containing fraction was then dialysed again using 0.05M phosphate-0.5M sodium chloride buffer of pH 7.2 and the resulting purified LPF-containing fraction retained. 3. Preparation of Agglutinogens 2 and 3 ($Ag_{2+3}$)

The centrifuged cellular fraction was washed using sterile pyrogen-free distilled water, centrifuged and then homogenized using 0.014M phosphate-0.14M sodium chloride buffer at pH 7.2. The homogenized bacterial suspension was then centrifuged at 9000 rpm to remove bacterial cells and the supernatant which contained Bordetella pertussis fimbrae retained. Ammonium sulphate was added to the supernatant to give a final concentration of 30% saturation and the suspension stored at 4° C. overnight to precipitate fimbrial proteins. After centrifuging at 9000 rpm the supernatant was discarded and the pellet extracted using pre-cooled phosphate buffer. The suspension was centrifuged at 15,000 rpm and the supernatant retained. The extraction was repeated four times and the resulting supernatants pooled.

Ammonium sulphate was added to the pooled supernatants to give a final concentration of 15% saturation and the resulting suspension stored overnight at 4° C. to precipitate fimbrial proteins.

The suspension was centrifuged at 15,000 rpm and the supernatant rejected.

The pellet was extracted with phosphate buffer and centrifuged at 15,000 rpm. The supernatant was collected and the extraction repeated four times and the resulting supernatants pooled.

Ammonium sulphate was added to the pooled supernatants to give a final concentration of 15% saturation and the resulting suspension stored overnight at 4° C. to precipitate fimbrial proteins. The suspension was centrifuged at 15,000 rpm and the supernatant rejected. (Further ammonium sulphate precipitations may be employed if necessary).

The pellet was extracted with phosphate buffer and centrifuged at 15,000 rpm. The supernatant was collected and the extraction repeated four times and the resulting supernatants pooled.

The pooled supernatant was then dialysed against phosphate buffer and subjected to membrane filtration.

4. Detoxification

All antigens were filtered through a Millex GV 0.22 um filter unit. The LPF preparation was diluted to a final protein concentration of 200 ug/ml using 0.05M phosphate-0.5M sodium chloride buffer at pH 7.2. A 40% formaldehyde solution was added to give a final concentration of formaldehyde of 0.5%. The LPF-containing fraction was then incubated at 37° C. for 14 days, inverting the contents at least once every 2 days to disperse any precipitate formed.

The resulting detoxified LPF fraction was then dialysed against PBS buffer containing 0.01% formaldehyde and 0.01% thiomersal and decanted into a container for storage, ensuring that all precipitated material has been transferred.

A similar detoxification procedure was applied to the FHA fraction and the agglutinogens 2 and 3 ($Ag_{2+3}$) fraction, except that the incubation at 37° C. was for 7 days.

The detoxified antigens in PBS containing 0.01% formaldehyde 0.01% thiomersal were mixed in equal proportions and diluted with sterile water, 4 x concentrated PBS containing 0.04% formaldehyde and 0.04% thiomersal and alhydogel. The resultant vaccine, in isotonic PBS, contains 120 ug protein/ml, 25% Alhydrogel, 0.01% formaldehyde and 0.01% thiomersal. As an alternative adjuvant to Alhydrogel, aluminium phosphate (added as aluminium chloride) may be employed. The vaccine can be further diluted with PBS, diptheria and tetanus toxoids and alhydrogel, to yield a concentration of pertussis antigens to 60 ug/ml.

The following yields of FHA, LPF and agglutinogens 2 and 3 ($AG_{2+3}$) were obtained from 18 liters of culture:

FHA—190 mg

LPF—50 mg agglutinogens 2 and 3 ($Ag_{2+3}$)—50 mg

We claim:

1. A process for the co-production of lymphocytosis promoting factor (LPF), filamentous haemagglutinin (FHA) and at least one fimbrial agglutinogen from a liquid culture of Bordetella pertussis, which comprises the steps of (a) separating the culture into cellular and supernatant fractions, (b) subsequent to step (a) concentrating the supernatant fraction to less than 50% of its original volume to form a concentrated aqueous supernatant fraction of reduced water content, (c) subsequent to step (b), fractionating the concentrated supernatant fraction to isolate LPF and FHA containing fractions, and (d) isolating at least one fimbrial agglutinogen from the cellular fraction.

2. A process according to claim 1 wherein the fimbrial agglutinogens isolated in step (d) include at least one of agglutinogens 2, 3, 4, 5 and 6.

3. A process according to claim 1 wherein the fimbrial agglutinogens isolated in step (d) comprise at least agglutinogens 2 and 3 ($Ag_{2+3}$).

4. A process according to claim 3 wherein the isolated agglutinogens additionally include one or more of agglutinogens 4, 5 and 6.

5. A process according to claim 1 wherein separation step (a) is carried out at a pH greater than 7.0.

6. A process according to claim 5 wherein separation step (a) is carried out at a pH in the range from 7.5 to 9.0.

7. A process according to claim 1 wherein in step (b) the supernatant is concentrated to less than 50% and preferably less than 25% of its original volume.

8. A process according to claim 1 wherein in step (c) the LPF containing fraction is purified by adsorption on fetuin sepharose followed by elution using a magnesium chloride buffer.

9. A process for the production of a vaccine composition comprising lymphocytosis promoting factor (LPF), filamentous haemagglutinin (FHA) and at least one fimbrial agglutinogen which comprises mixing (i) LPF, (ii) FHA and (iii) at least one fimbrial agglutinogens produced according to claim 1, the LPF, FHA and the at least one fimbrial agglutinogens being detoxified prior to or subsequent to mixing.

* * * * *